(12) United States Patent
Storari et al.

(10) Patent No.: US 11,766,368 B2
(45) Date of Patent: Sep. 26, 2023

(54) RIGID OR SEMI-RIGID PROTECTING ELEMENT FOR COVERING WOUNDS

(71) Applicant: Pharmadome S.r.l., Brescia (IT)

(72) Inventors: Alberto Storari, Negrar (IT); Cristian Fracassi, Bassano Bresciano (IT); Alessandro Romaioli, San Zeno Naviglio (IT); Stefano Cartapani, Brescia (IT)

( * ) Notice: Subject to any disclaimer, the term of this patent is extended or adjusted under 35 U.S.C. 154(b) by 0 days.

(21) Appl. No.: 15/733,229

(22) PCT Filed: Dec. 20, 2018

(86) PCT No.: PCT/IB2018/060443
§ 371 (c)(1),
(2) Date: Jun. 12, 2020

(87) PCT Pub. No.: WO2019/123376
PCT Pub. Date: Jun. 27, 2019

(65) Prior Publication Data
US 2020/0383850 A1 Dec. 10, 2020

(30) Foreign Application Priority Data
Dec. 20, 2017 (IT) .................. 102017000147076

(51) Int. Cl.
*A61F 15/00* (2006.01)

(52) U.S. Cl.
CPC .................... *A61F 15/008* (2013.01)

(58) Field of Classification Search
CPC .......... A61F 13/00017; A61F 13/00025; A61F 13/00046; A61F 13/00089; A61F 13/00548; A61F 13/00936; A61F 13/0266; A61F 13/025; A61F 13/00987; A61F 13/0246; A61F 13/0206; A61F 15/004; A61F 15/005; A61F 15/006; A61F 15/007; A61F 15/008; A61F 2013/00604; A61F 2013/00412; A61F 2013/00902; A61F 2013/00863; A61F 2013/00582; A61F 2013/00685; A61F 2013/00817; A61F 2013/00719;
(Continued)

(56) References Cited

U.S. PATENT DOCUMENTS 2,443,481 A * 6/1948 Leon ............... A61F 15/008
602/59
3,976,066 A 8/1976 McCartney
(Continued)

FOREIGN PATENT DOCUMENTS

DE 102008041785 3/2010
EP 2161011 A1 * 3/2010 ......... A61F 13/4915
(Continued)

*Primary Examiner* — Ophelia A Hawthorne
*Assistant Examiner* — Michael Milo
(74) *Attorney, Agent, or Firm* — Themis Law (57) ABSTRACT

A protecting element for wounds includes a rigid or semi-rigid substantially concave covering portion adapted to be anchored so as to face a wound and to be spaced therefrom, and anchoring members of the covering portion adapted to be anchored to the skin surrounding the wound to be protected. In particular, the anchoring members include at least one pair of movable fins that are independent from each other and are rotatably coupled to the covering portion.

8 Claims, 5 Drawing Sheets

(58) Field of Classification Search
CPC .. A61F 2013/00089; A61F 2013/00361; A61F 2013/00165; A61F 2013/0017; A61F 2013/00174; A61F 2013/00195; A61F 2013/002; A61F 2013/00182; A61F 2013/00919; A61F 2013/00914; A61F 2013/0091; A61F 2013/00846; A61F 2013/0074; A61F 2013/00757; A61F 2013/00565; A61F 2013/00561; A61F 2013/00387; A61F 2013/00212; A61F 2013/00859; A61F 2013/00834; A61F 7/007; A61F 2007/0088; A61F 2007/0078; A61F 2007/0071; A61M 25/02; A61M 2025/0206; A61M 2025/01213; A61M 2025/0246; A61M 2025/0253; A61M 2025/0266; A61B 46/23
USPC ......... 602/2, 14, 41, 43, 47, 52, 56, 57, 58; 604/180, 304, 308; 128/888, 889, 879, 128/892; 607/108, 114
See application file for complete search history.

(56) References Cited

U.S. PATENT DOCUMENTS

| | | | | |
|---|---|---|---|---|
| 4,000,737 A | * | 1/1977 | Horn | A61F 15/008 128/888 |
| 4,134,399 A | * | 1/1979 | Halderson | A61F 15/008 128/888 |
| 4,633,863 A | * | 1/1987 | Filips | A61M 25/02 128/877 |
| 4,972,829 A | | 11/1990 | Knerr | |
| 5,144,958 A | * | 9/1992 | Krueger | A61F 15/008 600/556 |
| 5,238,010 A | * | 8/1993 | Grabenkort | A61M 25/02 128/846 |
| 6,110,197 A | | 8/2000 | Augustine | |
| 2003/0069529 A1 | * | 4/2003 | Augustine | A61F 15/008 602/53 |
| 2004/0078011 A1 | | 4/2004 | Stevens | |
| 2004/0127838 A1 | | 7/2004 | Jeziak | |
| 2005/0222527 A1 | * | 10/2005 | Miller | A61M 1/964 602/1 |
| 2008/0195050 A1 | * | 8/2008 | Dickert | A61M 25/02 604/180 |
| 2010/0318052 A1 | * | 12/2010 | Ha | A61F 13/0226 604/385.01 |
| 2014/0221907 A1 | * | 8/2014 | Scholz | A61F 13/00051 604/25 |

FOREIGN PATENT DOCUMENTS

| | | | |
|---|---|---|---|
| KR | 200472060 Y1 * | 4/2014 | |
| WO | 201303713 | 3/2013 | |
| WO | 2013039713 | 3/2013 | |
| WO | 2016067015 | 5/2016 | |
| WO | WO-2016067015 A1 * | 5/2016 | ............ A61F 13/02 |
| WO | 2018085795 | 5/2018 | |

\* cited by examiner

RIGID OR SEMI-RIGID PROTECTING ELEMENT FOR COVERING WOUNDS

FIELD OF THE INVENTION

The present invention relates to a protecting element, and in particular it concerns an element for the protection of a skin area of a person, comprising a wound.

BACKGROUND OF THE INVENTION

It is known that in case of wounds, abrasions, excoriations or the like, it is necessary to protect the latter from dirt or infections, and at the same time it is necessary to prevent the clothing worn by a person from getting dirty because of the wound itself.

For this purpose, different types of elements for the protection of wounds to apply to the skin of the person, such as for example patches are well known. They comprise an adhesive part susceptible to be glued with the skin and a non-adhesive part susceptible to come into contact with the wound.

The patches, however, do not protect the wound from shocks, and coming into contact with the wound prevent it from recovering quickly.

For this purpose, rigid devices to be interposed between the wound and the bandage are well known to prevent the latter to come into contact with the same wound.

Some examples of such devices are known from US2004/127838, U.S. Pat. Nos. 4,972,829, 3,976,066 and 6,110,197.

Such known devices are poorly adaptable to the different morphology of the various areas of the human body, in particular to the curved areas, with the risk of being ineffective, annoying and/or with the risk of detaching easily.

SUMMARY OF THE INVENTION

Object of the present invention is to overcome, at least partially, the drawbacks illustrated above, by providing a protective element for wounds with a high functionality.

Another object of the invention is to provide a protecting element for wounds particularly inexpensive to make.

Another object of the invention is to provide a protecting element for wounds that is adaptable to different parts of the human body.

Such objects, as well as others that will be clearer hereinafter, are fulfilled by a protecting element for wounds according to what is herein described, shown and/or claimed.

The dependent claims define advantageous embodiments of the invention.

BRIEF DESCRIPTION OF THE DRAWINGS

Further features and advantages of the present invention will become more evident by reading the detailed description of some preferred but not exclusive embodiment of a protecting element 1, illustrated as a non-limiting example, with the help of the annexed drawings, wherein.

DETAILED DESCRIPTION OF SOME PREFERRED EMBODIMENTS

With reference to the above mentioned figures, it is here described a rigid or semi-rigid protecting element for wounds 1, which is susceptible to be anchored to the skin area of a person surrounding the wound F to protect.

It is understood that, even though hereinafter we will generally refer to a wound F, the protecting element may be equally used in case of abrasion, excoriation, infection, furuncle, acne, burn, tattoo or any similar event requiring protection and/or dressing, without departing from the scope of the invention defined in the appended claims.

As better explained below, the protecting element 1 may be configured so as, once it is applied to the skin of the person, the wound F does not come into contact with clothing or bandages, both to protect the wound and to prevent clothing or bandages from getting dirty due to blood, pus or medicaments.

The present invention comprises several similar or identical parts and/or elements. Where not otherwise specified, similar or identical parts and/or elements will be indicated with a single reference number, meaning that the technical characteristics described are common to all the similar or identical parts and/or elements.

The protecting elements 1 may comprise or may consist of a single laminar element in rigid or semi-rigid polymeric material, which may preferably be an optically transparent or translucent polymeric material. For example, such material may be polyethylene terephthalate (PET) or Polyvinyl Chloride (PVC).

The protecting element 1 may comprise at least one covering portion 2 substantially concave susceptible to remain facing the wound F and spaced apart the latter. It is understood that the concavity may be therefore facing the wound F.

In particular, the covering portion 2 may remain spaced apart the wound F and may present a plurality of base edges 5 susceptible to come into contact with the skin, preferably in a peripheral area with respect to the wound F itself.

The covering portion 2 may comprise an upper area 10 substantially planar or slightly curved and a plurality of peripheral areas 20, 20', each extending from the former in order to connect it to the respective section 6 of the respective base edge 5.

In particular, the covering portion 2 may comprise a couple of peripheral areas 20, preferably equal to each other, and possibly a couple of front and rear areas 20', preferably equal to each other as well.

Figure 7:
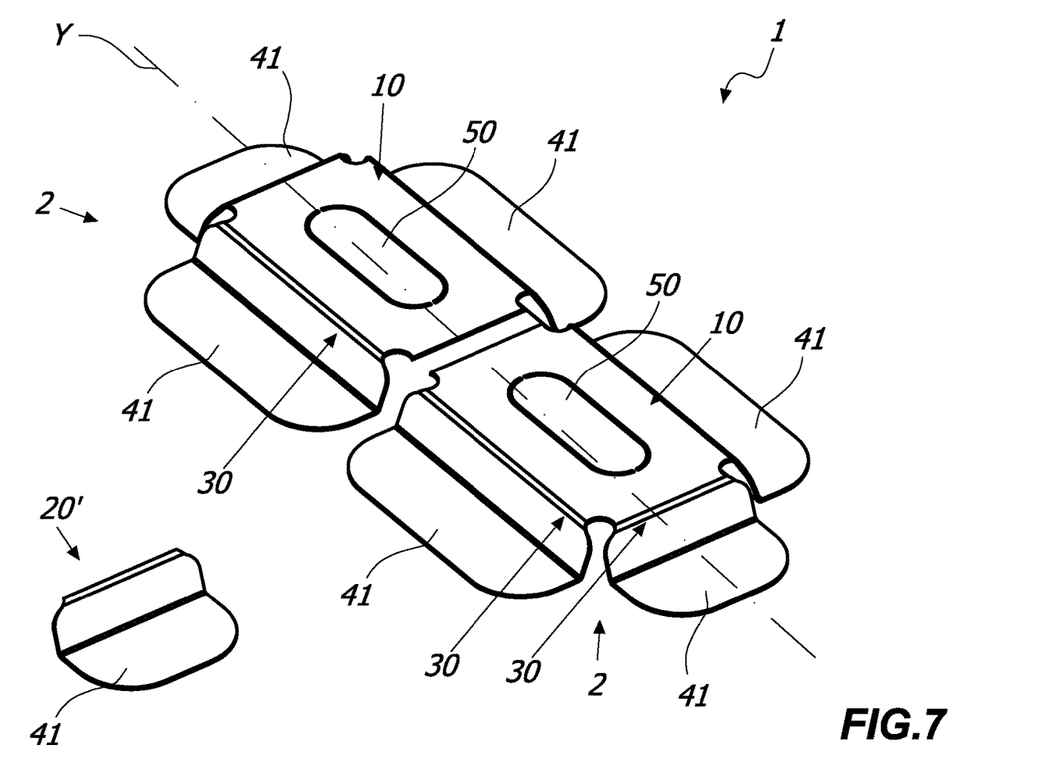
Figure 8:
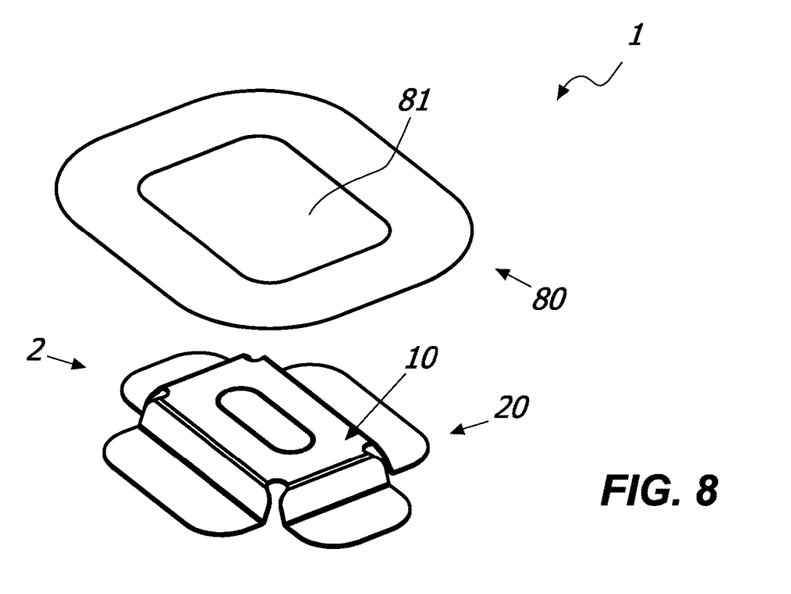
Figures 9A, 9B, 10:
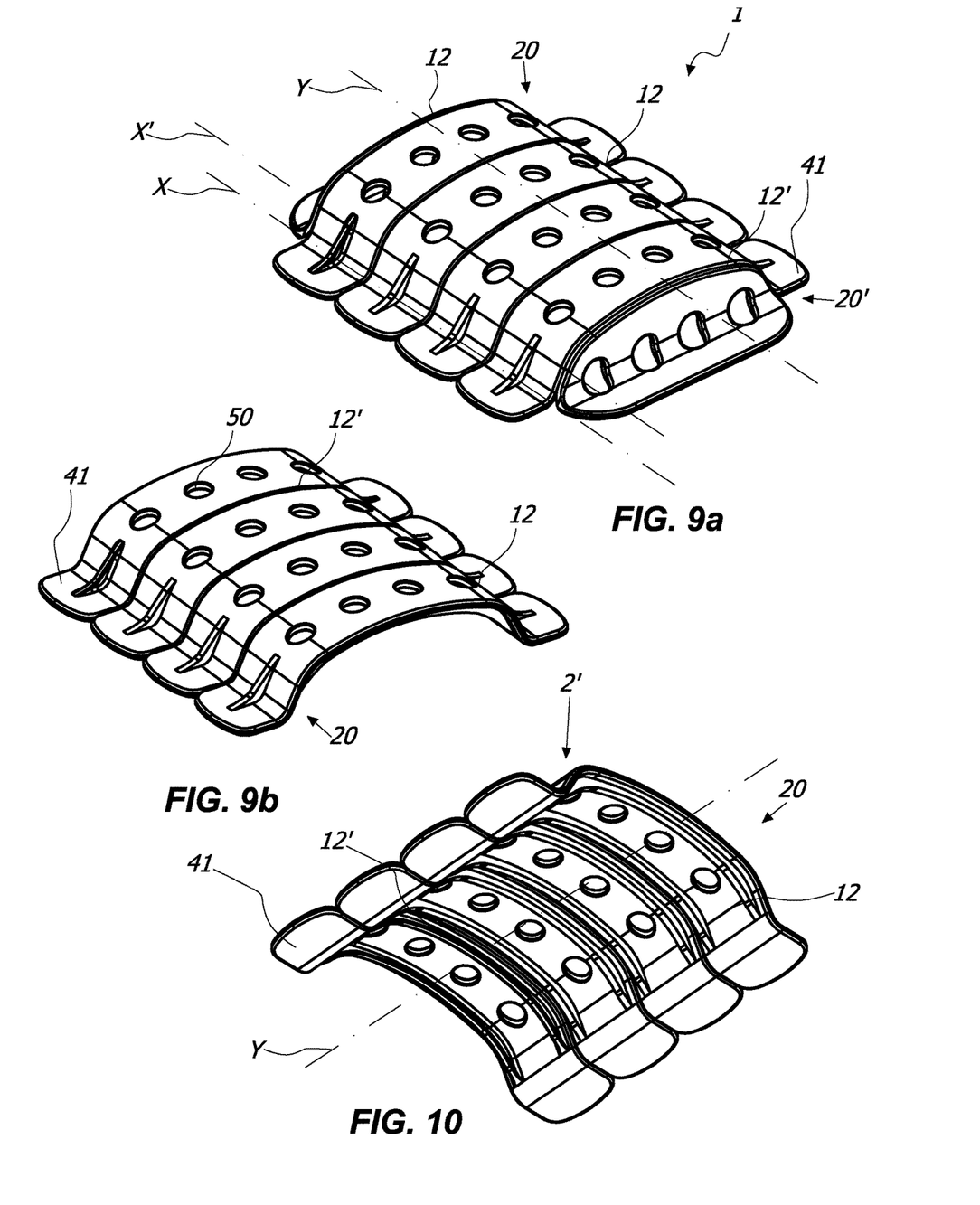
FIG. 9a is an axonometric view of a further embodiment of the protecting element 1.
FIG. 9b is a view of the embodiment of the protecting element 1 of FIG. 9a wherein the front area and rear area 20' have been removed.
FIG. 10 is an axonometric view of a further embodiment of the protecting element 1.

For example, the embodiment shown in FIGS. 1 to 9b comprises both the peripheral areas 20 and the front and rear areas 20', whereas the embodiment shown in FIG. 10 comprises the peripheral areas 20 only.

Figure 1:
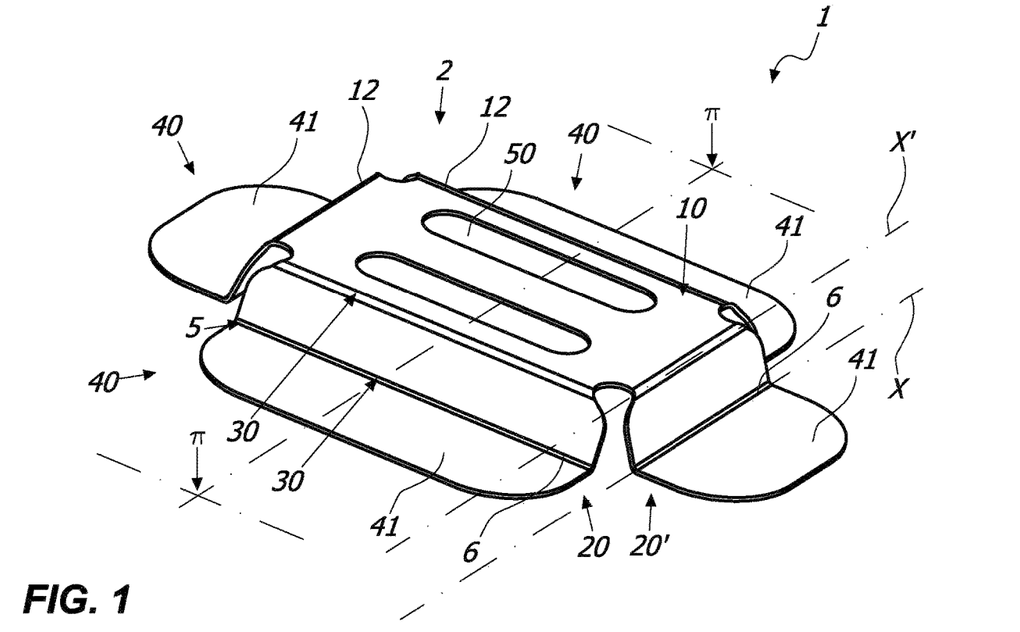
FIGS. 1, 2, 3, 4, 7 and 8 are axonometric views of different embodiments of a protecting element 1.
Figure 2:
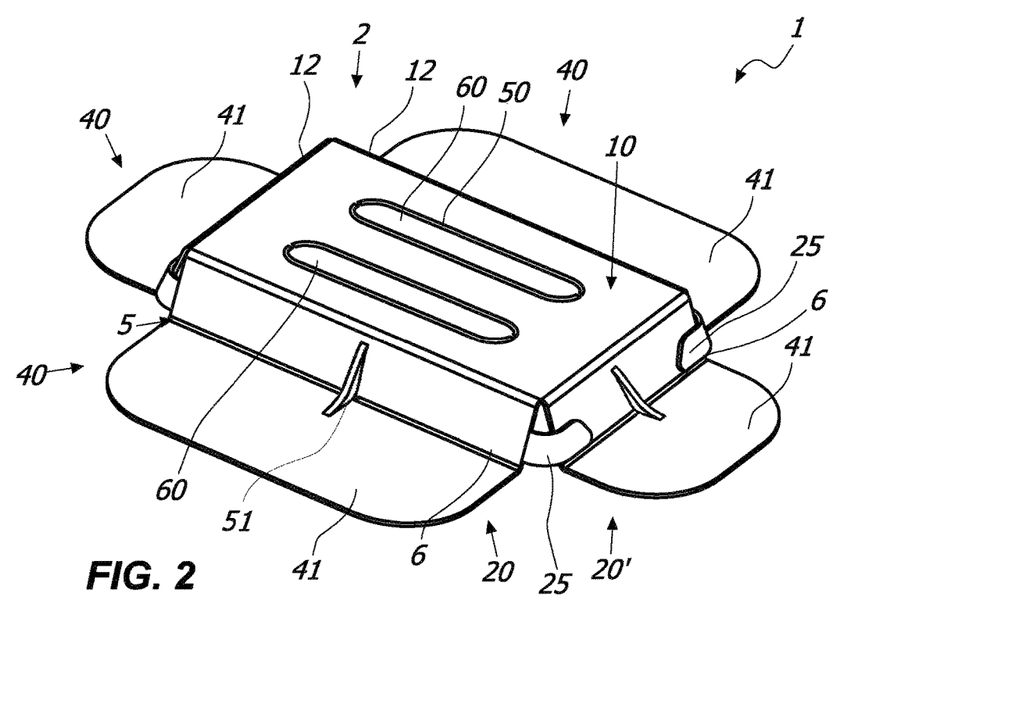
Figure 3:
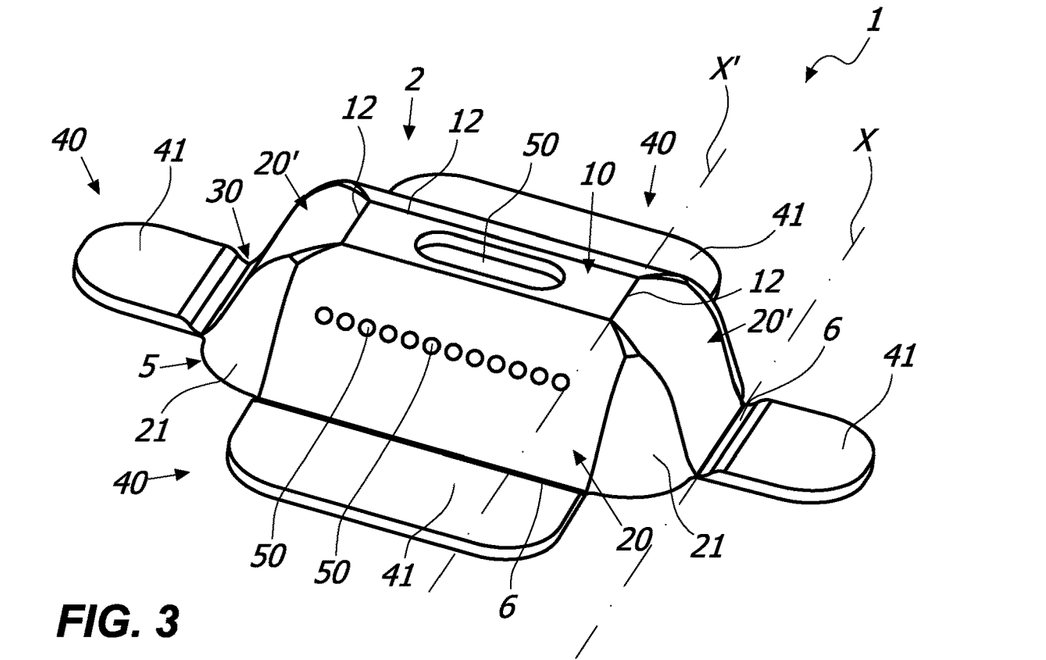
Figure 4:
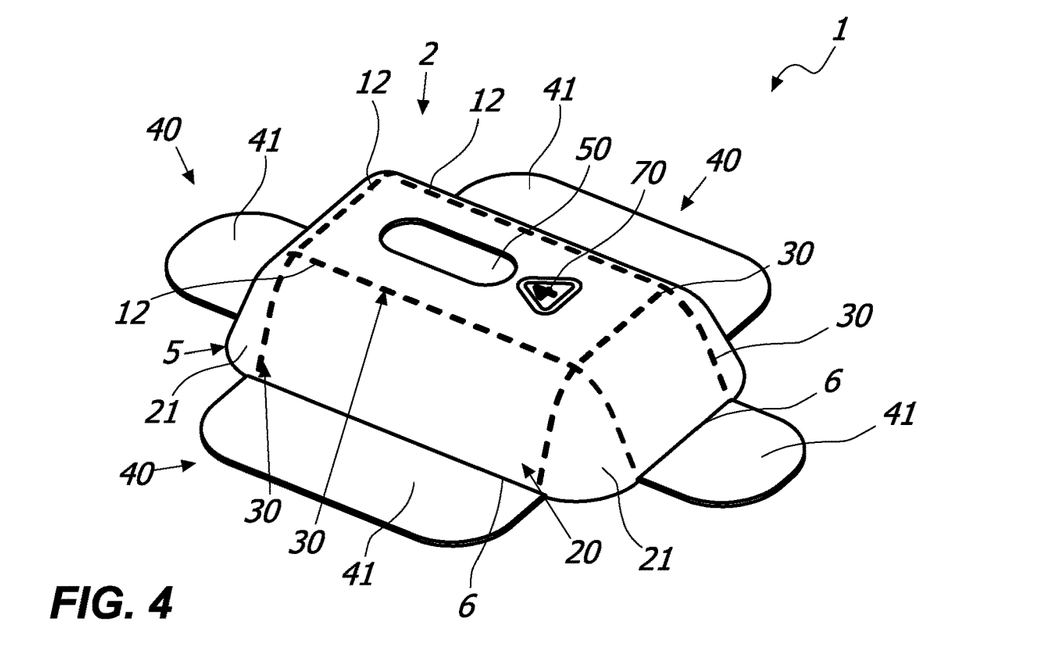
Figure 5:
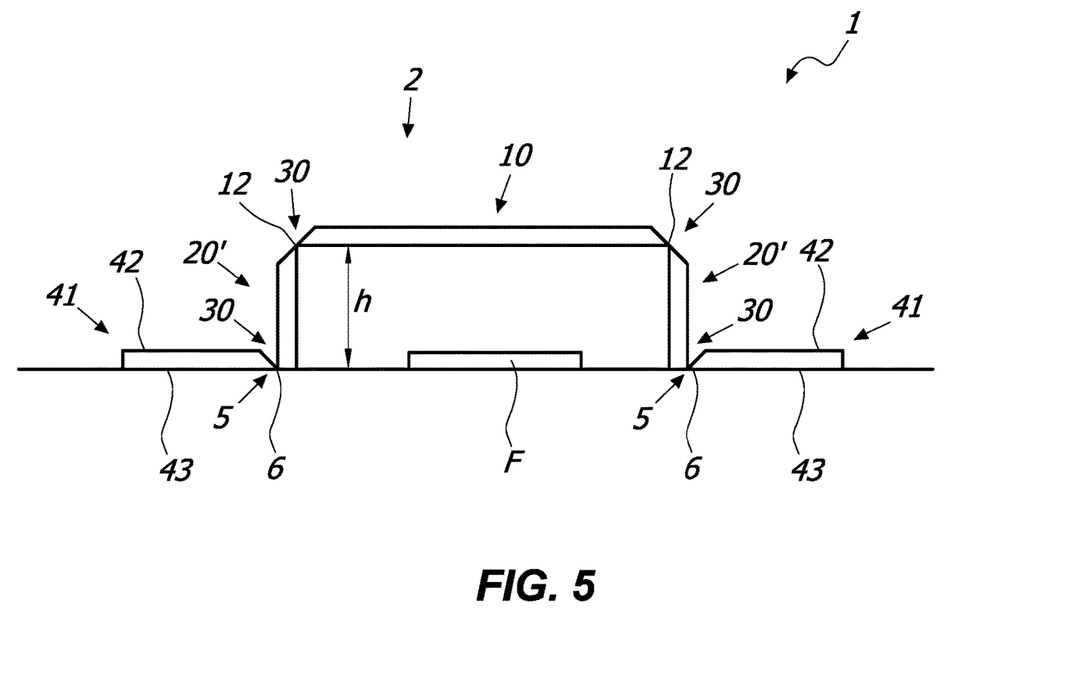
FIGS. 5 and 6 are schematic side views of different applications of an embodiment of the protecting element 1.
Figure 6:
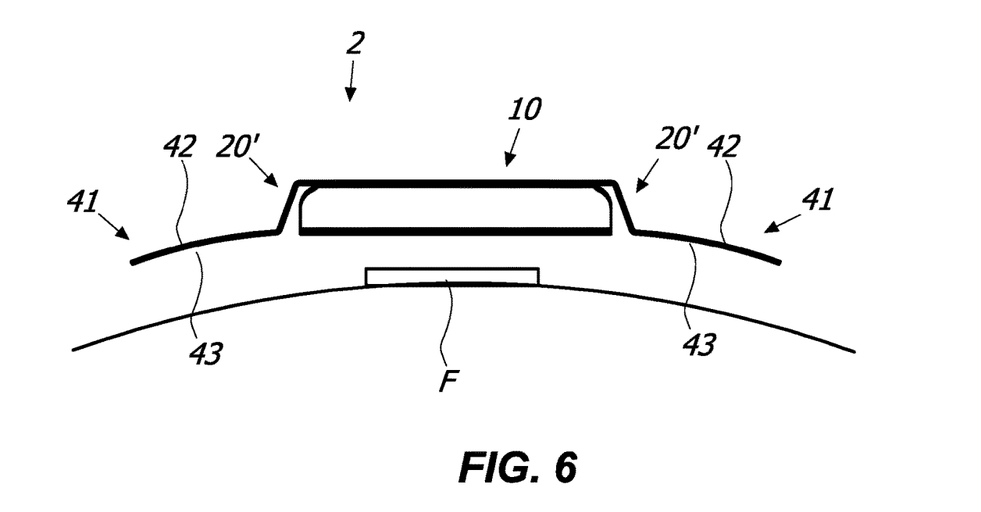

The peripheral areas 20 and the front and rear areas 20' may be substantially integral to each other, for example as shown in FIG. 3, or they may be interspersed with one or more discontinuities so as to be movable in a substantially independent manner, for example as shown in FIGS. 1 and 2.

Possibly, the peripheral areas 20 and the front and rear areas 20' may be connected by connecting elements 21, which may be selectively removed by the user or by the operator according to requirements.

According to a particular aspect of the invention, each peripheral area 20 and, if present, front and rear areas 20' may be rotatably coupled with the upper area 10 in at least one section 12 thereof.

In particular, the section 12 of the upper area 10 may define the longitudinal axis X' acting as a reciprocal rotation axis between the same upper area 10 and the respective peripheral 20 or front or rear area 20'.

In the embodiments shown in FIGS. 1 to 9b comprising both the peripheral areas 20 and the front and rear areas 20', the upper area 10 may have four sections 12 which substantially define the perimeter thereof.

On the other hand, the embodiment shown in FIG. 10 which comprises only the peripheral areas 20 may comprise a pair of sections 12 facing each other.

Preferably, the upper area 10 may have an elongated shape in order to define a main development axis Y. Possibly, the upper area 10 may have a substantially polygonal plan shape, preferably but not exclusively a substantially rectangular plan shape.

According to a particular preferred but not exclusive embodiment of the invention, the upper area 10 may be substantially planar or slightly curved in order to define a plane n and may be facing the wound F and spaced apart from the latter thanks to the peripheral areas 20, 20'.

Suitably, anchoring means 40 may be provided for anchoring the covering portion 10 to the skin surrounding the wound F to protect.

In particular, the anchoring means 40 may comprise at least one pair of fins 41, which may be movable independently to each other. Preferably, the fins 41 may be arranged on opposite sides with respect to the covering portion 2, in correspondence of the peripheral areas 20.

According to a particular aspect of the invention, the fins 41 may have an upper face 42 at sight and a lower face 43 susceptible to come into contact with the skin. In order to secure the fins 41 to the skin of the user, a bandage, a gauze, one or more patches or similar may be provided. Stiffening ribs 51 extend form the fins 41 to the peripheral areas 20 so as to enable the covering portion 2 to retain a distance from the wound.

Advantageously, each fin 41 may be rotatably coupled with the covering portion 2 in correspondence of the base edges 5 to reciprocally rotate.

In particular, the fins 41 may be rotatably coupled with the base edge 5 in at least one section 6 thereof.

The section 6 may define a longitudinal axis X acting as a reciprocal rotation axis of the fin 41 and of the covering portion 2. Suitably, the longitudinal axis X and the longitudinal axis X' may be substantially parallel to each other.

Such configuration allows to cover wounds F located in any position of the human body, even in the presence of curves or articulation. The independent mobility of the fins 41, indeed, will allow an excellent anchoring of the covering element 1 independently from the configuration of the area surrounding the wound F to cover.

For example, in case the protecting element 2 is anchored to the elbow, it may be allowed to bend the arm, avoiding the same protecting element 2 annoys and/or hinders the movement and avoiding the detaching from the skin of the same protecting element 2.

Such extreme adaptability is also allowed by the intrinsic flexibility of the polymeric material of which the covering element 1 is made of, which is flexible when needed, in order to adapt to the morphology of the area surrounding the wound F, but which nevertheless allows to always keep the upper area 10 spaced apart the latter of a height h.

Moreover, the possibility of rotation of the peripheral areas 20, and if present 20', allows to reduce or to increase this height h, depending on requirements. For example, it may be possible to increase this height h in case particular bulky dressings are necessary, or it may be possible to reduce it in order to limit the bulkiness or the discomfort of the same protecting element 1.

Suitably, the lower face 43 may be adhesive. For example, in a per se known manner, an adhesive tape coupled to the same lower face may be provided, otherwise a layer of glue or similar may be provided.

Possibly, a layer of adhesive material may be provided, such as an adhesive gauze, arranged on the lower faces 43 of the fins 41. In this manner, on the one hand it may be possible to promote the adherence of the protecting element 1 to the skin, and on the other hand it may be possible to make the contact between the protecting element and the skin itself more comfortable, in particular between the fins 41 and the skin.

Suitably, the covering portion 2 may comprise one or more sacrificial areas selectively separable therefrom.

In a preferred but not exclusive embodiment of the invention, such sacrificial areas may be defined by one or more of the peripheral areas 20 or front or rear areas 20'.

For example, in FIG. 7 two protecting elements 1 are shown, where the front area has been removed 20'. In this manner, it is possible to juxtapose or overcome the protecting elements along the axis Y, so as to cover wounds of any length.

On the other hand, in FIG. 9b a protecting element 1 is shown, where the front and rear areas have been removed 20', which are visible for example in FIG. 9a.

In such a situation as well, it is possible to juxtapose or overcome the protecting elements along the axis Y, so as to cover wounds of any length.

It is understood that it is possible to make the peripheral areas 20 removable, independently from the possibility to remove the front and rear areas 20'. In other words, the peripheral areas 20 and/or the front and rear ones 20' may define the sacrificial areas.

In this manner, it is possible to juxtapose or overcome the protecting elements both along the axis Y and in a direction perpendicular thereto, so as to cover any size of the wound F.

In a further embodiment shown in FIG. 10, the covering portion 2 may consist of a plurality of sections modularly placed side by side 2', all equal to each other, each defining a respective sacrificial area. In this case, the removal of one or more sacrificial areas 2' may allow to selectively change the size of the protecting element 1, and in particular the length thereof, considered along the axis Y.

For example, the latter may be sold with a predetermined number of sections, and its length may be reduced according to requirements, by removing one or more sacrificial areas or sections 2'.

It is understood that the covering portion 2 may have even just one part made of sections, for example the central part, and removable continuous areas, for example the front and rear ones, as shown in FIGS. 9a and 9b.

It is furthermore understood that the sacrificial areas 20 may be of any size, not necessarily equal to each other.

Therefore, it is clear that, thanks to the above mentioned characteristics, it may be possible to change the configuration of the protecting element according to the shape, size and/or location of the wound F to protect.

In order to facilitate the removal of the sacrificial areas, each of the latter may be operatively connected with the remaining part of the covering portion 2 by a separation line which comprises weakening means 30 of the laminar element of which the protecting element is made.

The separation lines may for example be the sections 12 in the embodiments shown in FIGS. 1 to 8 or the edges 12' in the embodiments shown in FIGS. 9a to 10.

The weakening means 30 may be of a per se known type. For example, they may be defined by a thinning of the covering portion 2 in correspondence of the separation lines, and/or by a plurality of passing through holes aligned along the latter.

Thanks to this features, it may be possible to reciprocally separate in a controlled manner the sacrificial areas from the remaining part of the covering portion 2 by acting along the respective separation line, for example by tearing or pulling.

Possibly, as shown in FIG. 2, stopping means 25, preferably of the removable type, may be provided in order to restrain the peripheral areas 20, 20' in an operative position so as even after shocks and/or bandages the protecting element 1 does not collapse, i.e. the upper area 10 remains spaced apart the wound F.

For example, the stopping means 25 may be tongues to connect two adjacent peripheral areas 20, 20' so as to prevent the rotation with respect to the upper area 10.

On the other hand, the peripheral areas 20 and, if present, the front and rear areas 20' may be disconnected from each other, so as to allow the maximum reciprocal independent mobility. In other words, the peripheral areas 20 and, if present, the front and rear areas 20' may be exclusively connected with the upper area 10 in correspondence of the respective sections 12, whereas they may be disconnected from each other.

According to a particular aspect of the invention, the covering portion 2 may comprise at least one hole 50 passing therethrough in order to allow the ventilation of the wound F and or the introduction of catheters, needles or similar. In particular, the holes 50 may be arranged on the upper area 10 and/or on one or more peripheral areas 20, 20'.

Suitably, the protecting element 1 may comprise at least one closing element 60 which may be coupled with the upper area 10 and/or the peripheral areas 20 in order to close one or more passing through holes 50. Preferably, the closing element 60 may be selectively removable by the user or by the operator, so as to allow a better ventilation of the wound F, according to requirements.

For example, a longitudinal passing through slot 50 or a couple of slots 50 placed on the upper area 10 and a sheet shaped element 60 of equal shaping coupled with the upper area 10 through two sacrificial points, may be provided.

According to another aspect of the invention, identification elements may be provided, for example in order to simply and quickly identify the size of the protecting element 1 or the intended use or other similar characteristics. The identification elements may be for example an embossed code, a writable area or the like, and they may be arranged in correspondence of the upper area 10 so as to be easily visible by the user or the operator. On the other hand, the identification element may be a R-FID tag, possibly embedded in the laminar element of which the protection element 1 is made.

Advantageously, as shown in FIG. 8 an adhesive element 80 may be provided in order to promote the adherence of the protective element 1 to the skin. In particular, the adhesive element 80 may have a substantially rectangular shape and it may have a central hole 81 so as to remain in correspondence of the faces 42 of the fins 41, i.e. only in correspondence of the peripheral areas 20, so that the upper area 10 remains substantially transparent.

According to a particular aspect of the invention, the protecting element 1 may be made by thermoforming or injection molding or by blanking and bending of a polymeric material sheet, so as to obtain the laminar element.

In this way the production costs of the protecting element 1 may be particularly low.

Moreover, according to a particular embodiment, the whole protecting element 1 may comprise the adhesive layer so as to simplify and speed up the processing operations.

The invention is susceptible to numerous modifications, all falling within the scope of protection of the attached claims. All the details may be replaced with other technically equivalent elements and the materials may be different according to requirements, without departing from the scope of the invention defined in the appended claims.

The invention claimed is:

1. A protecting element for wounds comprising:
   a single laminar element of rigid or semi-rigid polymeric material which includes:
   at least one concave covering portion comprising,
     an upper area that is planar or curved and is adapted to face a wound and be spaced therefrom,
     at least one pair of base edges adapted to come into contact with skin surrounding the wound, and
     at least one pair of peripheral areas each extending between the upper area and a respective base edge, and
   at least one pair of fins each extending from a respective base edge to anchor the at least one covering portion to the skin surrounding the wound to be protected, each fin comprising a lower face adapted to come into contact with the skin and an opposite upper face,
   wherein the at least one covering portion comprises at least one sacrificial area selectively separable therefrom so as to enable a variation of a configuration of the protecting element by disposing a plurality of sections side by side according to shape, size and/or position of the wound to be protected,
   wherein the at least one sacrificial area is operatively connected to a remaining part of the at least one covering portion by at least one separation line configured to weaken the single laminar element, so as to allow a reciprocal guided separation therefrom by action along the at least one separation line,
   wherein the upper area has an elongated shape so as to define a main development axis,
   wherein the at least one covering portion has the plurality of sections modularly placed side by side, each of the plurality of sections defining a respective sacrificial area, the plurality of sections being equal to each other, a removal of one or more of the sections providing for selectively modifying a size along a main development axis of the upper area,
   wherein the peripheral areas are facing each other and extend in a parallel manner to a main development axis of the upper area, a pair of front and rear areas extending perpendicularly to the peripheral areas, at least one of the peripheral areas and/or front and rear areas defining the at least one sacrificial area, a removal of the at least one sacrificial area allowing juxtaposing or overcoming two or more protection elements along the main development axis and/or perpendicularly thereto wherein each section comprises a plurality of stiffening ribs extending from one of the fins to one of the peripheral areas so as to enable the at least one covering portion to retain a distance from the wound after separation, and wherein a plurality of passing through holes is defined in each section so as to enable ventilation of the wound and introduction of a catheter, further comprising a bandage, a gauze for securing the at least one pair of fins to the skin of a user, or one or more patches for securing the at least one pair of fins to the skin of a user; and further comprising stopping means that restrain at least some of the peripheral areas to one another, wherein the tongues removably connect the adjacent peripheral areas.

2. The protecting element according to claim 1, wherein each fin is rotatably coupled with the respective base edge in at least one first section thereof that defines a first axis for a reciprocal rotation of the fin and the respective peripheral area.

3. The protecting element according to claim 2, wherein each of the peripheral areas is rotatably coupled with the upper area in at least one second section of the upper area that defines a second axis for a reciprocal rotation of the upper area and the respective peripheral area, the first and the second axis being parallel to each other.

4. The protecting element according to claim 1, wherein the separation line configured to weaken the single laminar element by a thinning of the laminar element at the separation line and/or by having a plurality of passing through holes aligned along the separation line.

5. The protecting element according to claim 1, wherein the upper area has a quadrangular plan shape.

6. The protecting element according to claim 1, further comprising at least one closing element coupled with the plurality of passing through holes so as to protect the plurality of passing through holes, the at least one closing element being selectively removable by a user or an operator.

7. The protecting element according to claim 1, wherein the polymeric material is optically transparent or translucent.

8. The protecting element according to claim 1, wherein the stopping means are configured as tongues that connect adjacent peripheral areas.

* * * * *